United States Patent [19]

Kondo et al.

[11] Patent Number: 4,812,585
[45] Date of Patent: Mar. 14, 1989

[54] PROCESS FOR PRODUCING 2-ACEYLFURAN DERIVATIVES

[75] Inventors: Michitada Kondo, Kobe; Masayoshi Minai, Moriyama; Seiichi Kai, Nara; Takayuki Higashii, Kishiwada; Yuji Ueda, Izumi, all of Japan

[73] Assignee: Sumitomo Chemical Company, Limited, Osaka, Japan

[21] Appl. No.: 108,467

[22] Filed: Oct. 15, 1987

[30] Foreign Application Priority Data

Oct. 28, 1986 [JP] Japan .................. 61-257637
Oct. 28, 1986 [JP] Japan .................. 61-257638

[51] Int. Cl.⁴ .......................................... C07D 307/46
[52] U.S. Cl. ...................................... 549/483; 549/488
[58] Field of Search ............................. 549/483, 488

[56] References Cited

U.S. PATENT DOCUMENTS 2,515,123  7/1950  Hartough ..................... 549/483
2,963,488 12/1960  Webb ........................... 549/488
4,254,043  3/1981  Kuta ............................ 549/483

OTHER PUBLICATIONS

Journal of Organic Chemistry, vol. 28, No. 3, Mar. 22, 1963, pp. 674–679, W. R. Edwards et al, "Mixed Carboxylic Anhydrides in the Friedel–Crafts Reaction".

Primary Examiner—Richard L. Raymond
Attorney, Agent, or Firm—Stevens, Davis, Miller & Mosher

[57] ABSTRACT

2-Acylfuran derivatives

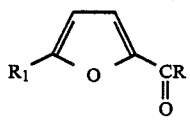

($R$: alkyl, phenyl, etc.; $R_1$: H, alkyl) are prepared in high yield by reaction, in the presence of a boron trifluoride complex catalyst, of a furan compound

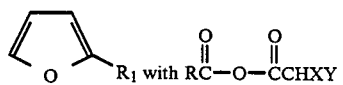

(X: H, Cl, Br; Y: Cl, Br) or with RCOOH in the presence of $(XYCHCO)_2O$.

22 Claims, No Drawings

PROCESS FOR PRODUCING 2-ACEYLFURAN DERIVATIVES

The present invention relates to a process for producing 2-acylfuran derivatives represented generally by the following formula;

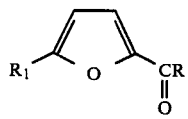

wherein R is typically alkyl or phenyl group and $R_1$ is hydrogen or alkyl group.

The 2-acylfuran derivatives are very important as intermediates of medicines or of agricultural chemicals, particularly as an intermediate of prostaglandings.

For producing such 2-acylfuran derivatives, various processes have hitherto been known, and the typical processes are exemplified below:

(a) J.C.S., 2262 (1982)

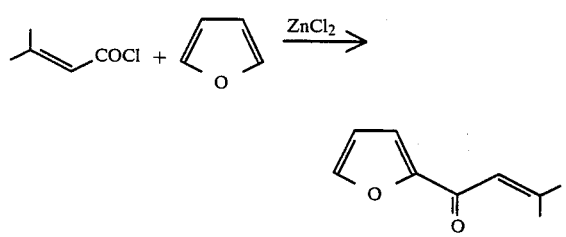

(b) J.C.S., 2723 (1963)

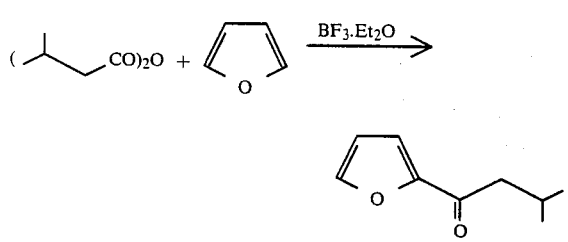

(c) U.S. Pat. No. 4,254,043

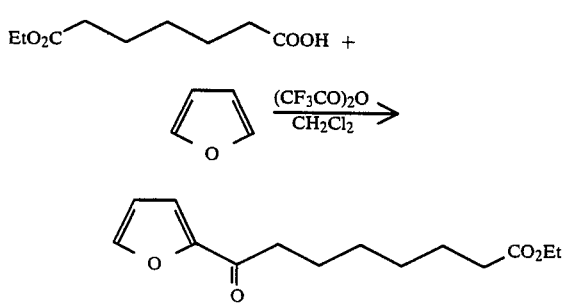

These processes mentioned above, however, are not always industrially satisfactory because the yield is low in processes (a) and (b), and reagents used for the reaction are very expensive in process (c).

Accordingly, it is an object of the present invention to provide process for producing 2-acylfuran derivatives represented generally by the above-mentioned formula in high yield, and advantageously to industries concerned.

According to the present invention, there is provide a process for producing 2-acylfuran derivatives represented by the formula (I);

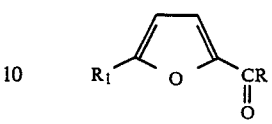

(I)

wherein R is an alkyl group having 1 to 18 carbon atoms, an alkenyl group having 3 to 8 carbon atoms, an alkynyl group having 3 to 8 carbon atoms, a cyclic alkyl group having 4 to 7 carbon atoms, phenyl group, a phenyl group having one or two substituents selected from the group consisting of alkyl groups having 1 to 5 carbon atoms, alkoxyl groups having 1 to 5 carbon atoms and halogen atoms, an aralkyl group having 7 to 12 carbon atoms, an alkyl group having 2 to 8 carbon atoms which has a substituent of an alkoxyl group having 1 to 5 carbon atoms, or an alkyl group having 2 to 8 carbon atoms which has a substituent of an alkoxycarbonyl group having 2 to 6 carbon atoms; and $R_1$ is hydrogen atom or a lower alkyl group; which comprises reacting, in a solvent and in the presence of a boron trifluoride complex catalyst, a furan compound represented by the formula (II);

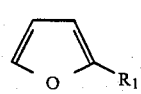

(II)

wherein $R_1$ has the same meaning as defined above, with either (a) a mixed acid anhydride represented by the formula (III);

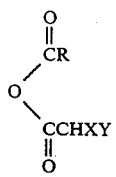

(III)

wherein R has the same meaning as defined above, X is hydrogen, chlorine or bromine atom, and Y is chlorine or bromine atom, or with (b) a carboxylic acid represented by the formula (IV);

RCOOH (IV)

wherein R has the same meaning as defined above in the presence of an acid anhydride represented by the formula (V);

(XYCHCO)$_2$O (V)

wherein X and Y have the same meanings as defined above.

Preferred solvents used in the present invention include aromatic hydrocarbons such as benzene, toluene, xylene and the like; and halogenated hydrocarbons such as carbon tetracloride, dichloromethane, dichloroethane, tetrachloroethylene, monochlorobenzene and the like. These are used alone or in combination of two or more, and the amount of such solvent is not critical.

As the catalyst, boron trifluoride or a boron trifluoride complex is used, and the boron trifluoride complex includes boron trifluoride-diethyl ether complex, boron trifluoride-methanol complex, boron trifluorideacetic acid complex, and the like.

Furan compounds used in the present invention include furan, 2-methylfuran, 2-ethylfuran and the like.

In the process of (a) mentioned above, though the amount of catalyst to be used is generally from 0.05 to 1 equivalents based on the mixed acid anhydride (III), the reaction proceeds even in an amount of catalyst of from 0.05 to 0.15. The amount of furan compound (II) is necessarily 1.0 or more equivalents, preferably from 1.2 to 2 equivalents based on the mixed acid anhydride (III). The reaction temperature is in a range of generally from $-5°$ to $100°$ C., preferably from $30°$ to $70°$ C. The reaction time is generally in a range of from 0.5 to 20 hours, but it to not particularly limited.

The mixed acid anhydride represented by the formula (III), which is one of starting materials for the above-mentioned reaction, can be produced by reacting a carboxylic acid represented by the formula (VI);

RCOOH              (VI)

wherein R has the same meaning as defined above, with a haloacetic acid compound represented by the formula (VII);

XYCHCOZ            (VII)

wherein Z is hydroxyl group, chlorine or bromine atom, and X and Y are as defined above.

The carboxylic acid represented by the formula (VI) includes aliphatic carboxylic acids having 1 to 18 carbon atoms such as acetic acid, propionic acid, butyric acid, isobutyric acid, valeric acid, isovaleric acid, hexanoic acid, heptanoic acid, octanoic acid, lauric acid, decanoic acid, stearic acid, and the like; unsaturated aliphatic carboxylic acids having 3 to 8 carbon atoms such as acrylic acid, crotonic acid, trans-2-pentenoic acid, 4-pentenoic acid, trans-2-hexanoic acid, trans-3-hexanoic acid, cis-3-hexanoic acid, trans-2-methyl-2-pentenoic acid, 4-pentynoic acid and the like; saturated alicyclic carboxylic acids having 4 to 8 carbon atoms such as cyclopentane carboxylic acid, cyclohexane carboxylic acid and the like; such aromatic carboxylic acids being unsubstituted or mono- or di-substituted by alkyl group having 1 to 3 carbon atoms, alkoxyl group having 1 to 3 carbon atoms or halogen atom, such as benzoic acid, 4-methylbenzoic acid, 2,4-dimethylbenzoic acid, 4-methoxybenzoic acid, 4-bromobenzoic acid and the like; aralkyl carboxylic acids having 7 to 12 carbon atoms such as phenylacetic acid, 3-phenylpropionic acid, 2-methyl-2-phenylacetic acid and the like; aliphatic carboxylic acids having 2 to 8 carbon atoms which are substituted by alkoxyl group having 1 to 5 carbon atoms or alkoxycarbonyl group having 2 to 6 carbon atoms such as 3-methoxypropionic acid, 5-ethoxypentanoic acid, butoxypentanoic acid, 6-methoxyhexanoic acid, succinic acid monoethyl ester, glutaric acid monomethyl ester, suberic acid monomethyl ester and the like.

When a haloacetic acid of the formula (VII) in which substituent Z is hydroxyl group, is used as the haloacetic acid compound, the aimed mixed acid anhydride can be obtained by the dehydration reaction in the presence or absence of a dehydrating agent, however, the aimed compound is easily available by the reaction using a haloacetyl halide in which the substituent Z is chlorine or bromine atom in the presence of an organic base and in a solvent. In the latter reaction, the amount of haloacetyl halide is generally from 1 to 1.5 equivalents based on the carboxylic acid. The organic base used in this reaction includes triethylamine, pyridine, diethylaniline and the like, and the amount thereof is generally from 1 to 1.5 equivalents based on the carboxylic acid. The reaction temperature is generally in a range of from $-20°$ to $50°$ C. The reaction time is generally in a range of from 0.5 to 10 hours, but it is not particularly limited.

The reaction mixture obtained is subjected to filtration for separating off the resulting hydrochloride or hydrobromide salt of organic base to obtain crude solution of the mixed acid anhydride, which is then purified to obtain the mixed acid anhydride. The crude solution mentioned above can be used as it is for the next reaction with a furan compound. Accordingly, it is advantageous to use a solvent same as the solvent used in the next step.

In the case of the process (b) mentioned above, same carboxylic acids as exemplified for carboxylic acids of (VI) may be used, and the acid anhydride (V) includes, for example, chloroacetic anhydride, bromoacetic anhydride, dichloroacetic anhydride and the like. The amount of furan compound (II) is necessarily 1.0 equivalent or more, preferably from 1.2 to 1.5 equivalents based on the carboxylic acid (IV). The amount of acid anhydride (V) is 1.0 equivalent or more, preferably from 1.1 to 1.3 equivalents based on the carboxylic acid (IV). Although the amount of the the boron trifluoride or boron trifuluoride complex catalyst is generally from 0.12 to 0.2 equivalents based on the carboxylic acid (IV), this amount is not restrictive and may be used in an amount of more than the above-mentioned amount. The reaction temperature is generally in a range of from $-5°$ to $150°$ C, preferably from $15°$ to $75°$ C. The reaction time is generally in a range of from 0.5 to 20 hours, but it is not particularly limited.

The reaction mixture thus obtained is post-treated in usual manners and then purified by methods such as distillation, column chromatography or the like, if necessary, to obtain in high yield the aimed 2-acylfuran derivatives(I).

Thus, according to the present invention, aimed 2-acylfuran derivatives (I) can be produced advantageously for the industry from a furan compound (II) and a mixed acid anhydride (III) or a carboxylic acid (IV). Moreover, since boron trifluoride, boron trifuloride complexes and acid anhydrides are commercially available cheeply, industrial value of the present invention is enhanced further.

The present invention will be described in more detail below by way of Examples.

EXAMPLE 1

A four neck flask equipped with a stirrer and a thermometer was charged with 9.41 g (0.05 mole) of suberic acid monomethyl ester, 5.11 g (0.0505 mole) of triethylamine and 60 ml of carbon tetrachloride. Under stirring, 5.71 g (0.0505 mole) of monochloroacetyl chloride was added dropwise thereto at 0° to 5° C. After completion of dropping, the reaction was continued at room temperature for 3 hours. After completion of the reaction, the reaction mixture was filtered under reduced pressure to remove formed hydrochloride salt of triethylamine.

To the filtrate were added 5.11 g (0.075 mole) of furan and 0.71 g (0.005 mole) of boron trifluoridediethyl ether complex and the resulting mixture was heated at 40° C. for 4 hours. After completion of the reaction, the reaction solution was cooled and washed successively with 50 ml of water, 50 ml of 5% aqueous sodium carbonate solution and 50 ml of water. The organic layer was dried over anhydrous magnesium sulfate and then concentrated under reduced pressure to obtain a crude product. The crude product was distilled under reduced pressure to obtain 9.75 g of pale yellow liquid 2-(7-methylcarbonyl1-oxoheptyl)furan.

Yield: 81.8% b.p.: 134°–136° C./0.32–0.35 mmHg.

EXAMPLE 2

A four neck flask equipped with a stirrer and a thermometer was charged with 9.41 g (0.05 mole) of suberic acid monomethyl ester, 5.06 g (0.05 mole) of triethylamine and 60 ml of carbon tetrachloride. Under stirring, 7.37 g (0.05 mole) of dichloroacetyl chloride was added dropwise thereto at 0 to 5° C. After completion of dropping, the stirring was continued at room temperature for 3 hours. After completion of the reaction, the reaction mixture was filtered under reduced pressure to remove formed hydrochloride salt of triethylamine.

To the filtrate were added 5.11 g (0.075 mole) of furan and 0.71 g (0.005 mole) of boron trifluoridediethyl ether complex in this order and the resulting mixture was then stirred at 50° C. for 2 hours. After completion of the reaction, the reaction mixture was cooled and washed successively with 50 ml of water, 50 ml of 5% aqueous sodium carbonate solution and 50 ml of water. The organic layer was dried over anhydrous magnesium sulfate and then concentrated under reduced pressure to obtain 10.65 g of a crude product. The crude product was distilled under reduced pressure to obtain 9.5 g of pale yellow oily 2-(7-methoxycarbonyl-1-oxoheptyl) furan.

Yield: 79.7% b.p.: 134°–136° C./0.32–0.35 mmHg.

EXAMPLE 3

A four neck flask equipped with a stirrer and a thermometer was charged with 6.51 g (0.05 mole) of heptanoic acid, 5.11 g (0.0505 mole) of triethylamine and 60 ml of carbon tetrachloride. Thereto was added 5.71 g (0.05 mole) of monochloroacetylchloride dropwise at 0 to 5° C. After completion of dropping, the stirring was continued at room temperature for 3 hours. After completion of the reaction, the reaction mixture was filtered under reduced pressure to remove formed hydrochloride salt of triethylamine.

To the filtrate were added 5.11 g (0.075 mole) of furan and 0.71 g (0.005 mole) of boron trifluoridediethyl ether complex and stirring was continued at 50° C. for 3 hours. After completion of the reaction, the reaction solution was cooled and washed successively with water, 5% aqueous sodium carbonate solution and water. The organic layer was concentrated under reduced pressure and the resulting concentrated residue was purified by silica gel-filled column chromatography to obtain 7.6 g of 2-hepanoylfuran.

Yield: 85%

$n_D^{25}$: 1.4820

EXAMPLES 4 to 16

Reaction and post-treatment were carried out in the same manner as in Example 1, except that each carboxylic acid (0.05 mole) shown in Table 1 was a substituent for suberic acid monomethyl ester in Example 1, to obtain results shown in Table 1.

TABLE 1

| Example No. | Starting carboxylic acid | | Produced 2-acylfuran derivative | | | |
|---|---|---|---|---|---|---|
| | Name of compound | Amount used | Amount produced | Yield | Name of compound | Physical properties |
| 4 | Pentanoic acid | 5.11 (g) | 6.2 (g) | 82 (%) | 2-Valerylfuran | $n_D^{25}$ 1.4860 |
| 5 | Isovaleric acid | 5.11 | 6.3 | 83 | 2-Isovalerylfuran | $n_D^{25}$ 1.4815 |
| 6 | Propionic acid | 3.7 | 3.1 | 50 | 2-Propionylfuran | $n_D^{25}$ 1.4908 |
| 7 | Succinic acid monoethyl ester | 7.31 | 7.46 | 76 | 2-(3-Ethoxycarbonyl-1-oxopropyl)furan | m.p. 52° C. |
| 8 | Benzoic acid | 6.11 | 4.13 | 48 | 2-Benzoylfuran | $n_D^{25}$ 1.5796 |
| 9 | Glutaric acid monomethyl ester | 7.31 | 7.65 | 78 | 2-(4-Methoxycarbonyl-1-oxobutyl)furan | m.p. 42.5° C. |
| 10 | 3-Phenylpropionic acid | 7.51 | 8.36 | 83.5 | 2-(1-Oxo-3-phenylpropyl)furan | $n_D^{25}$ 1.5633 |
| 11 | Cyclohexane carboxylic acid | 6.41 | 7.26 | 81.5 | Cyclohexyl furyl ketone | m.p. 41° C. |
| 12 | 6-Methoxyhexanoic acid | 7.31 | 7.9 | 81 | 2-(6-Methoxyhexanoyl)furan | $n_D^{25}$ 1.5132 |
| 13 | Crotonic acid | 4.31 | 2.66 | 39 | 2-Crotonylfuran | $n_D^{25}$ 1.4287 |
| 14 | Trans-3-hexenoic acid | 5.71 | 8.21 | 83 | 2-(Trans-3-hexenoyl)furan | $n_D^{25}$ 1.4291 |
| 15 | 4-Pentynyric acid | 4.71 | 6.22 | 84 | 2-(4-Pentynoyl)furan | $n_D^{25}$ 1.4368 |
| 16 | Stearic acid | 14.2 | 13.5 | 81 | 2-(Octadecanoyl)furan | $n_D^{25}$ 1.5144 |

EXAMPLE 17

Reaction and post-treatment were carried out in the same manner as in Example 1, except that 1.0 g of boron trifluoride-acetic acid complex was substituent for the boron trifluoride-diethyl ether complex, to obtain 8.53 g of 2-(7-methoxycarbonyl-1-oxoheptyl)furan.

Yield: 80% b.p.: 135°–137° C./0.35 mmHg

EXAMPLE 18

Reaction and post-treatment were carried out in the same manner as in Example 1, except that 8.61 g (0.05 mole) of decanoic acid was substituent for the suberic acid monomethyl ester, to obtain 9.15 g of 2-decanoylfuran.

Yield: 82.4%

$n_D^{25}$: 1.4998

EXAMPLE 19

A four neck flask equipped with a stirrer and a thermometer was charged with 3.7 g (0.05 mole) of propionic acid, 5.11 g (0.0505 mole) of triethylamine and 60 ml of carbon tetrachloride. Thereto was added dropwise 5.71 g (0.0505 mole) of monochloroacetyl chloride at 0° to 5° C. After completion of dropping, the reaction mixture was filtered under reduced pressure to remove formed hydrochloride salt of triethylamine.

To the filtrate were added 5.36 g (0.065 mole) of 2-methylfuran and 0.71 g of boron trifluoride-diethyl ether complex and the resulting mixture was stirred at 50° C. for 4 hours. After completion of the reaction, post-treatment was carried out in the same manner as in Example 3 to obtain 2.87 g of 2-propionyl-5-methylfuran.
Yield: 41.5%
$n_D^{25}$: 1.5087

EXAMPLE 20

Reaction and post-treatment were carried out in the same manner as in Example 19, except that 6.51 g (0.05 mole) of heptanoic acid was substituent for the propionic acid, to obtain 5.95 g of 2-heptanoyl-5-methylfuran.
Yield: 66%
$n_D^{25}$: 1.4910

EXAMPLE 21

In 50 ml of toluene were dissolved 9.41 g (0.05 mole) of suberic acid monomethyl ester and 9.83 g (0.0575 mole) of monochloroacetic anhydride. To the resulting solution were added 4.43 g (0.065 mole) of furan and 0.71 g of boron trifluoride-diethyl ether complex and the resulting mixture was then stirred at 50° C. for 6 hours. After completion of the reaction, the reaction solution was cooled and washed successively with of water, 5% aqueous sodium carbonate solution and water. The organic layer was dried over anhydrous magnesium sulfate and then concentrated under reduced pressure and the resulting concentrated residue was purified by silica gel-filled column chromatography to obtain 11 g of 2-(7-methoxycarbonyl-1-oxoheptyl)furan.
Yield: 92.3%
b.p.: 135°–137° C./0.35 mmHg.

EXAMPLE 22

In 50 ml of toluene were dissolved 6.51 g (0.05 mole) of heptanoic acid and 10.26 g (0.06 mole) of monochloroacetic anhydride. To the resulting solution were added 4.43 g (0.065 mole) of furan and 0.71 g of boron trifluoride-diethyl ether complex and the resulting mixture was then stirred at 50° C. for 5.5 hours. After completion of the reaction, the reaction solution was cooled and washed with 5% aqueous sodium carbonate solution and water in this order. The organic layer was concentrated under reduced pressure and the resulting concentrated residue was then purified by silica gel-filled column chromatography to obtain 8.2 g of 2-heptanoylfuran.
Yield: 91%
$n_D^{25}$: 1.4824

EXAMPLES 23 to 32

Reaction and post-treatment were carried out in the same manner as in Example 22, except that each carboxylic acid (0.05 mole) shown in Table 2 was substituent for the heptanoic acid, to obtain results shown in Table 2.

In Example 27, however purification by column chromatography was not carried out.

TABLE 2

| Example No. | Starting carboxylic acid | | Reaction condition | | Produced 2-acylfuran derivative | | | |
|---|---|---|---|---|---|---|---|---|
| | Name of compound | Amount used | Temperature | Time | Amount produced | Yield | Name of Compound | Physical properties |
| 23 | 3-Methylbutanoic acid | 5.11 (g) | 50 °(C.) | 5 (hrs) | 6.74 (g) | 88.6 (%) | 2-Isovalerylfuran | $n_D^{27.8}$ 1.4803 |
| 24 | n-Pentanoic acid | 5.11 | 50 | 5 | 6.76 | 88.8 | 2-Valerylfuran | $n_D^{28}$ 1.4865 |
| 25 | 2-Methylpropionic acid | 4.41 | 40 | 8 | 5.6 | 81.1 | 2-Isobutyrylfuran | $n_D^{28}$ 1.4870 |
| 26 | Propionic acid | 3.7 | 60 | 3 | 3.29 | 53 | 2-Propionylfuran | $n_D^{28}$ 1.4942 |
| 27 | Succinic acid monoethyl acid | 8.21 | 50 | 6 | 7.86 | 80.1 | 2-(3-Methoxycarbonyl-1-oxopropyl)furan | m.p. 51.6° C. |
| 28 | Benzoic acid | 6.11 | 50 | 8.5 | 4.13 | 48 | 2-Benzoylfuran | $n_D^{28}$ 1.5799 |
| 29 | Glutaric acid monomethyl ester | 7.31 | 50 | 6 | 8.07 | 82.3 | 2-(4-Methoxycarbonyl-1-oxobutyl)furan | m.p. 42.8° C. |
| 30 | Cyclohexane carboxylic acid | 6.41 | 50 | 6 | 7.75 | 87 | Cyclohexyl furyl ketone | m.p. 41° C. |
| 31 | n-Butyric acid | 4.41 | 50 | 6 | 4.07 | 58.9 | 2-Butyrylfuran | $n_D^{27.8}$ 1.4598 |
| 32 | 3-Phenylpropionic acid | 7.51 | 50 | 6 | 9.06 | 90.5 | 2-(1-oxo-3-phenylpropyl)furan | $n_D^{26.2}$ 1.5636 |

EXAMPLE 33

In 50 ml of toluene were dissolved 3.7 g (0.05 mole) of propionic acid and 10.26 g (0.06 mole) of monochloroacetic anhydride. To the resulting solution were added 5.36 g (0.065 mole) of 2-methylfuran and 0.71 g of boron trifluoride-diethyl ether complex and the resulting mixture was then stirred at 50° C. for 7 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 2.96 g of 2-propionylfuran.
Yield: 42.8%
$n_D^{25}$: 1.5078

EXAMPLE 34

In 50 ml of toluene were dissolved 6.51 g (0.05 mole) of heptanoic acid and 10.26 g (0.06 mole) of monochloroacetic anhydride. To the resulting solution were added 5.34 g (0.065 mole) of 2-methylfuran and 0.71 g of boron trifluoride-diethyl ether complex and the resulting mixture was then stirred at 50° C. for 5.5 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 6.27 g of 2-heptanoyl-5-methylfuran.
Yield: 69.6%
$n_D^{25}$: 1.4900

EXAMPLE 35

In 50 ml of toluene were dissolved 6.51 g (0.05 mole) of heptanoic acid, 4.43 g (0.065 mole) of furan and 14.39 g (0.06 mole) of dichloroacetic anhydride. To the resulting solution was added 0.71 g of boron trifluoridediethyl ether coplex and the resulting mixture was then stirred at 50° C. for 3 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 8.95 g of 2-heptanoylfuran.

Yield: 99.3%
$n_D^{25}$: 1.4823

EXAMPLE 36

In 50 ml of toluene were dissolved 7.31 g (0.05 mole) of monomethylglutaric acid, 4.43 g (0.085 mole) of furan and 14.39 g (0.06 mole) of dichloroacetic anhydride. To the resulting solution was added 0.71 g of boron trifluoride-diethyl ether complex and the resulting mixture was then stirred at 50° C. for 3 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 9.54 g of 2-(4-methoxycarbonylbutyryl)furan.

Yield: 94.5%
m.p.: 42.5° C.

EXAMPLE 37

In 50 ml of toluene were dissolved 4.41 g (0.05 mole) of isobutyric acid, 5.34 g (0.065 mole) of 2-methylfuran and 14.39 g (0.06 mole) of dichloroacetic anhydride. To the resulting solution was added 0.71 g of boron trifluoride-diethyl ether complex and the resulting mixture was then stirred at 50° C. for 3 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 6.74 g of 2-isobutyryl-5-methylfuran.

Yield: 88.6%
$n_D^{25}$: 1.4939

EXAMPLE 38

In 50 ml of toluene were dissolved 7.31 g (0.05 mole) of 6-methoxyhexanoic acid, 4.43 g (0.065 mole) of furan and 14.39 g (0.06 mole) of dichloroacetic anhydride. To the resulting solution was added 0.71 g of boron trifluoride-diethyl ether complex and the resulting mixture was then stirred at 50° C. for 3 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 8.83 g of 2-(6-methoxyhexanoyl)furan.

Yield: 90%
$n_D^{25}$: 1.5132

EXAMPLE 39

In 50 ml of toluene were dissolved 4.31 g (0.05 mole) of crotonic acid, 4.43 g (0.065 mole) of furan and 10.26 g (0.06 mole) of monochloroacetic anhydride. To the resulting solution was added 0.71 g of boron trifluoridediethyl ether complex and the resulting mixture was then stirred at 50° C. for 6.5 hours. After completion of the reaction, the reaction solution was cooled and washed successively with water, 5% aqueous sodium carbonate solution and water. The organic layer was concentrated under reduced pressure and the resulting concentrated residue was then purified by silica gel-filled column chromatography to obtain 2.8 g of 2-crotonylfuran.

Yield: 41.1%
$n_D^{25}$: 1.4283

EXAMPLE 40

In 50 ml of toluene were dissolved 9.41 g (0.05 mole) of suberic acid monomethyl ester and 9.83 g (0.0575 mole) of monochloroacetic anhydride. To the resulting solution were added 4.43 g (0.065 mole) of furan and 1.0 g of boron trifluoride-acetic acid complex and the resulting mixture was then stirred at 60° C. for 3 hours. After completion of the reaction, the reaction solution was cooled and washed successively with 5% aqueous sodium carbonate solution and water. The organic layer was concentrated under reduced pressure and the resulting concentrated residue was then purified by silica gel-filled column chromatography to obtain 10.1 g of 2-(7-methoxycarbonyl-1-oxoheptyl)furan.

Yield 85%.
b.p.: 135°–137° C./0.35 mmHg.

EXAMPLES 41 to 44

Reaction and post-treatment were carried out in the same manner as in Example 40, except that each carboxylic acid (0.05 mole) shown in Table 3 was substituent for the suberic acid monomethyl ester, to obtain results shown in Table 3.

TABLE 3

| | Starting carboxylic acid | | Produced 2-acylfuran derivative | | | |
|---|---|---|---|---|---|---|
| Example No. | Name of compound | Amount used | Amount produced | Yield | Name of compound | Physical properties |
| 41 | 4-Pentynoic acid | 4.9 (g) | 6.5 (g) | 88 (%) | 2-(4-Pentynoyl)furan | $n_D^{25}$ 1.4356 |
| 42 | Trans-3-hexonoic acid | 5.7 | 6.57 | 80 | 2-(Trans-3-hexenoyl)furan | $n_D^{25}$ 1.4308 |
| 43 | Decanoic acid | 8.6 | 10.55 | 95 | 2-Decanoylfuran | $n_D^{25}$ 1.4986 |
| 44 | Stearic acid | 14.2 | 15.2 | 91.3 | 2-Octadecanoylfuran | $n_D^{25}$ 1.5146 |

We claim:

1. A process for producing 2-acylfuran derivatives represented by the formula;

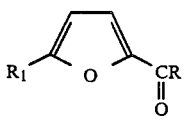

wherein R is an alkyl group having 1 to 18 carbon atoms, an alkenyl group having 3 to 8 carbon atoms, an alkynyl group having 3 to 8 carbon atoms, a cyclic alkyl group having 4 to 7 carbon atoms, phenyl group, a phenyl group having one or two substituents selected from the group consisting of alkyl groups having 1 to 5 carbon atoms, alkoxyl groups having 1 to 5 carbon atoms and halogen atoms, an aralkyl group having 7 to 12 carbon atoms, an alkyl group having 2 to 8 carbon atoms which has a substituent of an alkoxyl group having 1 to 5 carbon atoms, or an alkyl group having 2 to 8 carbon atoms which has a substituent of an alkoxycarbonyl group having 2 to 6 carbon atoms; and $R_1$ is hydrogen atom or a lower alkyl group, which comprises reacting, in a solvent and in the presence of a boron trifluoride or a boron trifluoride complex catalyst, a furan compound represented by the formula;

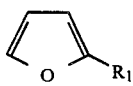 (I)

wherein $R_1$ has the same meaning as defined above, with either (a) a mixed acid anhydride represented by the formula;

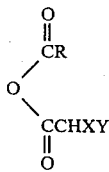

wherein R has the same meaning as defined above, X is hydrogen, chlorine or bromine atom, and Y is chlorine or bromine atom, or with (b) a carboxylic acid represented by the formula;

RCOOH wherein R has the same meaning as defined above, in the presence of an acid anhydride represented by the formula;

(XYCHCO)$_2$O wherein X and Y have the same meanings as defined above.

2. A process according to claim 1, wherein said solvent is an aromatic hydrocarbon or a halogenated hydrocarbon.

3. A process according to claim 1, wherein said boron trifluoride complex is boron trifluoride-diethyl ether complex, boron trifluoride-acetic acid complex or boron trifluoride-methanol complex.

4. A process according to claim 1, wherein the amount of said catalyst is from 0.05 to 1 equivalents based on said mixed acid anhydride.

5. A process according to claim 1, wherein the amount of acid catalyst is from 0.02 to 0.2 equivalents based on said carboxylic acid.

6. A process according to claim 1, wherein the amount of said furan compound is from 1.2 to 2 equivalents based on said mixed acid anhydride.

7. A process according to claim 1, wherein the amount of said furan compound is from 1.2 to 2 equivalents based on said carboxylic acid.

8. A process according to claim 1, wherein the amount of said acid anhydride is from 1.1 to 1.3 equivalents based on said carboxylic acid.

9. A process according to claim 1, wherein said mixed acid anhydride represented by the formula;

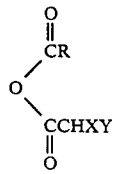

wherein R, X and Y are as defined above, is produced by reacting a carboxylic acid represented by the formula;

RCOOH wherein R is as defined above, with a haloacetic acid compound represented by the formula:

XYCHCOZ wherein X is hydrogen, chlorine or bromine atom, Y is bromine or chlorine atom, and Z is hydroxyl group, chlorine or bromine atom.

10. A process according to claim 1 or 9, wherein said carboxylic acid is an aliphatic carboxylic acid having 1 to 18 carbon atoms.

11. A process according to claim 1 or 9, wherein said carboxylic acid is an unsaturated aliphatic carboxylic acid having 3 to 8 carbon atoms.

12. A process according to claim 1 or 9, wherein said carboxylic acid is a saturated alicyclic carboxylic acid having 4 to 8 carbon atoms.

13. A process according to claim 1 or 9, wherein said carboxylic acid is benzoic acid.

14. A process according to claim 1 or 9, wherein said carboxylic acid is a benzoic acid substituted by one or two alkyl groups having 1 to 3 carbon atoms, alkoxyl groups having 1 to 3 carbon atoms or halogen atoms.

15. A process according to claim 1 or 9, wherein said carboxylic acid is an aralkyl carboxylic acid having 7 to 12 carbon atoms.

16. A process according to claim 1 or 9, wherein said carboxylic acid is an aliphatic carboxylic acid having 2 to 8 carbon atoms substituted by alkoxyl group having 1 to 5 carbn atoms.

17. A process according to claim 9, wherein the substituent Z of said haloacetic acid compound is chlorine or bromine atom.

18. A process according to claim 17, wherein said reaction is carried out in the presence of an organic base.

19. A process according to claim 18, wherein said organic base is triethylamine, pyridine or diethylaniline.

20. A process according to claim 17, wherein the amount of said haloacetic acid compound is from 1 to 1.5 equivalents based on said carboxylic acid.

21. A process according to claim 18, wherein the amount of said organic base is from 1 to 1.5 equivalents based on said carboxylic acid.

22. A process according to claim 17, wherein the reaction temperature is in a range of from −20 to 50° C.

* * * * *

UNITED STATES PATENT AND TRADEMARK OFFICE

CERTIFICATE OF CORRECTION

PATENT NO. : 4,812,585
DATED : MARCH 14, 1989
INVENTOR(S) : MICHITADA KONDO ET AL

It is certified that error appears in the above-identified patent and that said Letters Patent is hereby corrected as shown below:

COLUMN 4, LINE 30, CHANGE "1.2 to 1.5" to --1.2 to 2.0--.

COLUMN 4, LINE 36, CHANGE "0.12 to 0.2" to

--0.02 to 0.2--.

Signed and Sealed this

Twelfth Day of March, 1991

Attest:

HARRY F. MANBECK, JR.

*Attesting Officer*   *Commissioner of Patents and Trademarks*